(12) United States Patent
Sherman

(10) Patent No.: US 12,048,784 B2
(45) Date of Patent: Jul. 30, 2024

(54) FRAGRANCE DIFFUSER WITH EMBODIED LIGHTING SYSTEM

(71) Applicant: David Sherman, Niagara on the Lake (CA)

(72) Inventor: David Sherman, Niagara on the Lake (CA)

( * ) Notice: Subject to any disclaimer, the term of this patent is extended or adjusted under 35 U.S.C. 154(b) by 0 days.

(21) Appl. No.: 18/143,109

(22) Filed: May 4, 2023

(65) Prior Publication Data

US 2023/0364293 A1 Nov. 16, 2023

Related U.S. Application Data

(60) Provisional application No. 63/341,452, filed on May 13, 2022.

(51) Int. Cl.
| | |
|---|---|
| *A61L 9/00* | (2006.01) |
| *A61L 9/03* | (2006.01) |
| *F21L 4/02* | (2006.01) |
| *F21S 8/00* | (2006.01) |
| *F21V 23/04* | (2006.01) |

(52) U.S. Cl.
CPC ............. *A61L 9/03* (2013.01); *F21L 4/027* (2013.01); *F21S 8/035* (2013.01); *F21V 23/0464* (2013.01); *F21V 23/0471* (2013.01); *A61L 2209/12* (2013.01)

(58) Field of Classification Search
CPC ........ A61L 9/03; A61L 2209/12; F21L 4/027; F21S 8/035; F21V 23/0464; F21V 23/0471
See application file for complete search history.

(56) References Cited

U.S. PATENT DOCUMENTS

| | | | |
|---|---|---|---|
| 10,060,582 B2* | 8/2018 | O'Brien | F21L 4/085 |
| 2009/0180271 A1* | 7/2009 | Jachmann | H05B 47/11 |
| | | | 362/183 |
| 2017/0119918 A1* | 5/2017 | Lima | H05B 3/141 |
| 2021/0178003 A1* | 6/2021 | Li | F21S 8/035 |
| 2022/0230532 A1* | 7/2022 | Myoung | A61L 9/03 |

* cited by examiner

*Primary Examiner* — Gerald J Sufleta, II

(57) ABSTRACT

An apparatus to produce a fragrance with an emergency flashlight and night light. The apparatus includes a fragrance dispenser, an emergency flashlight, a night light, and microprocessors. The fragrance dispenser dispenses fragrance through the evaporation of a liquid contained in a wick which was absorbed from the liquid in an attachable and replaceable bottle. The emergency flashlight is removeable and rechargeable. The emergency flashlight illuminates a plurality of LEDs automatically upon a power outage. The emergency removeable flashlight also contains an emergency light source. The night light operates in darkness. The microprocessors control the operation of the fragrance dispenser, the emergency light source and the night light.

12 Claims, 13 Drawing Sheets

FRAGRANCE DIFFUSER WITH EMBODIED LIGHTING SYSTEM

FIELD OF INVENTION

The present invention is generally related to a fragrance dispensing system and method thereof

BACKGROUND OF INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in-and-of-themselves may also be inventions.

Many fragrance dispenser systems and methods are commercially available for use to dispense essential oils and other fragrances into varying premises such as living areas, bedrooms, relaxation spaces, offices, and the like. Prior art is, quoted as U.S. Pat. No. 11,248,761 which presents a small night light lamp with spreading fragrance function. Also patent 2005/0185392 presents a coordinated emission of fragrance, light, and sound. However, these stated patents and various available fragrance dispensers do not provide emergency lighting, in the event of power outage or other emergencies.

Thus, in view of the above, there is a long-felt need in the industry to address the aforementioned deficiencies and inadequacies.

SUMMARY OF THE INVENTION

A fragrance dispensing system and method thereof are provided substantially, as shown in and/or described in connection with at least one of the figures, as set forth more completely in the claims.

The fragrance dispensing system herein presented includes a fragrance dispenser, an emergency flashlight and a motion activated night light. This dispensing system will produce a pleasant scent of varying fragrances, using separate, attachable, refillable scent bottles. The dispenser can include a switch to control the flow rate of scent and can optionally include a timing switch to control the period of fragrance dispensing operating time. The night light illuminates during dark periods when motion is sensed. A motion sensor and a plurality of LEDs can be embodied in the apparatus base or embodied in the removeable emergency flashlight.

In an aspect, the flashlight is rechargeable.
In an aspect, the base and the flashlight are separate.
In an aspect, the present fragrance dispensing system will plug into a building's electrical system.

These features and advantages of the present disclosure may be appreciated by reviewing the following description of the present disclosure, along with the accompanying figures wherein like reference numerals refer to like parts.

BRIEF DESCRIPTION OF DRAWINGS

The accompanying drawings illustrate the embodiments of devices, systems, methods, and other aspects of the disclosure. Any person with ordinary skills in the art will appreciate that the illustrated element boundaries (e.g., boxes, groups of boxes, or other shapes) in the figures represent an example of the boundaries. In some examples, one element may be designed as multiple elements, or multiple elements may be designed as one element. In some examples, an element shown as an internal component of one element may be implemented as an external component in another and vice versa. Furthermore, the elements may not be drawn to scale.

Various embodiments will hereinafter be described in accordance with the appended drawings, which are provided to illustrate, not limit, the scope, wherein similar designations denote similar elements, and in which.

DETAILED DESCRIPTIONS

The present disclosure is best understood with reference to the detailed figures and description set forth herein. Various embodiments have been discussed with reference to the figures. However, those skilled in the art will readily appreciate that the detailed descriptions provided herein with respect to the figures are merely for explanatory purposes, as the methods and systems may extend beyond the described embodiments. For instance, the teachings presented, and the needs of a particular application may yield multiple alternative and suitable approaches to implement the functionality of any detail described herein. Therefore, any approach may extend beyond certain implementation choices in the following embodiments.

References to "one embodiment," "at least one embodiment," "an embodiment," "one example," "an example,"

"for example," and so on indicate that the embodiment(s) or example(s) may include a particular feature, structure, characteristic, property, element, or limitation but that not every embodiment or example necessarily includes that particular feature, structure, characteristic, property, element, or limitation. Further, repeated use of the phrase "in an embodiment" does not necessarily refer to the same embodiment.

Methods of the present invention may be implemented by performing or completing manually, automatically, or a combination thereof, selected steps or tasks. The term "method" refers to manners, means, techniques, and procedures for accomplishing a given task including, but not limited to, those manners, means, techniques, and procedures either known to or readily developed from known manners, means, techniques, and procedures by practitioners of the art to which the invention belongs. The descriptions, examples, methods, and materials presented in the claims and the specification are not to be construed as limiting but rather as illustrative only. Those skilled in the art will envision many other possible variations within the scope of the technology described herein.

The present specification describes a novel apparatus which embodies a combination of a fragrance dispensing system, a motion sensor night light and an emergency flashlight.

Figure 1:
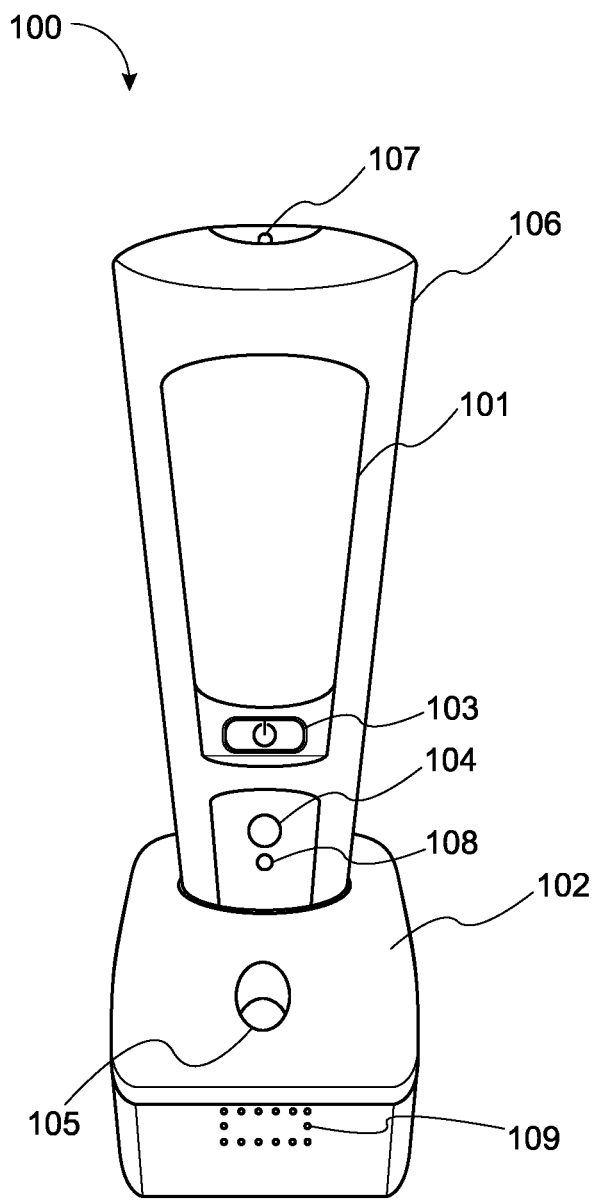
FIG. 1 illustrates a perspective view of a fragrance dispenser with a removeable emergency flashlight, in accordance with at least one embodiment.

FIG. 1 illustrates a perspective view 100 of the presented fragrance dispenser, with removeable emergency flashlight, in accordance with at least one embodiment. FIG. 1 depicts a light diffusing lens 101, a charging base 102, a switch 103, a motion sensor 104, a charging base hole 105, a removeable emergency flashlight 106, an emergency light source 107, a photocell 108, and an internal microprocessor 109.

Figure 2A:
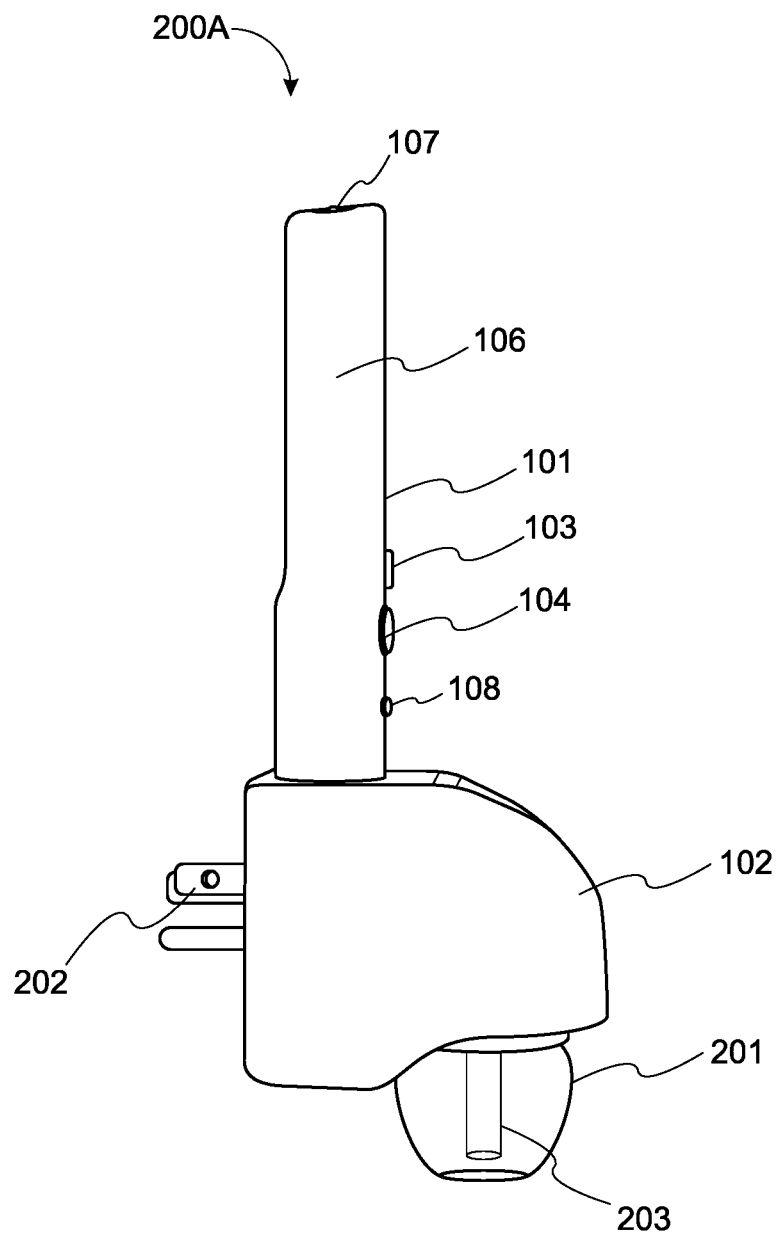
FIG. 2A illustrates a side view of a fragrance dispenser with a removeable emergency flashlight, in accordance with at least one embodiment.

FIG. 2A illustrates a side view 200A of the presented fragrance dispenser, with removeable flashlight, in accordance with at least one embodiment. FIG. 2A depicts a light diffusing lens 101, a charging base 102, a switch 103, a motion sensor 104, a removeable emergency flashlight 106, an emergency light source 107, a photocell 108, a fragrance bottle 201, a 3-prong electrical plug 202, and a wick 203.

Figure 2B:
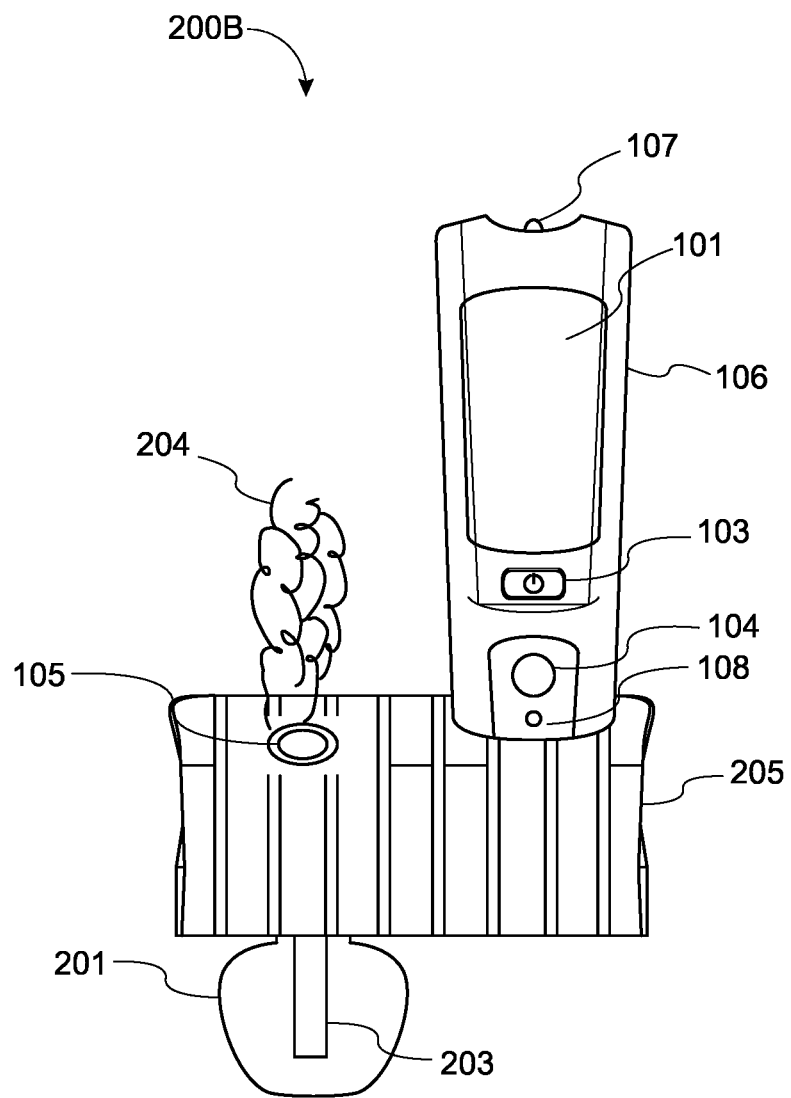
FIG. 2B illustrates a front view of an additional design of a fragrance dispenser with removeable emergency flashlight, in accordance with at least one embodiment.

FIG. 2B illustrates a front view 200B of an additional design of the presented fragrance dispenser, with removeable emergency flashlight, in accordance with at least one embodiment. FIG. 2B depicts a light diffusing lens 101, a switch 103, a motion sensor 104, a charging base hole 105, an emergency removeable flashlight 106, an emergency light source 107, a photocell 108, a fragrance bottle 201, a wick 203, an airborne fragrance 204, and a charging base 205.

Figure 2C:
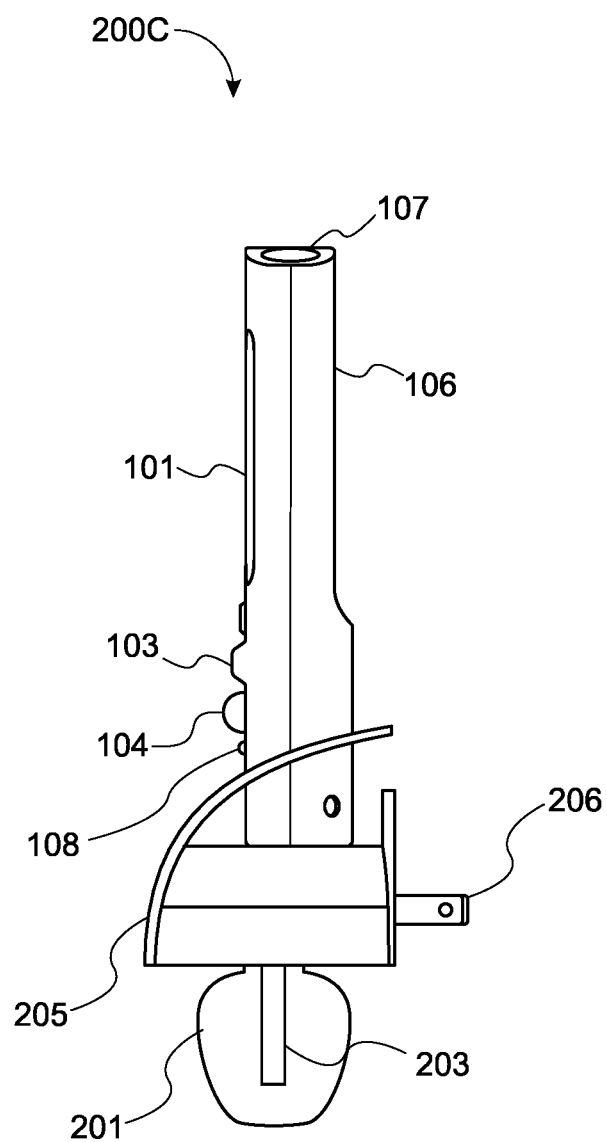
FIG. 2C illustrates, a side view of an additional design of a fragrance dispenser with removeable emergency flashlight, in accordance with at least one embodiment.

FIG. 2C illustrates a side view 200C of an additional design of the presented fragrance dispenser, with removeable emergency flashlight, in accordance with at least one embodiment. FIG. 2C depicts a light diffusing lens 101, a switch 103, a motion sensor 104, a removeable emergency flashlight 106, an emergency light source 107, a photocell 108, a fragrance bottle 201, a wick 203, a charging base 205, and a 2-prong plug 206.

Figure 3:
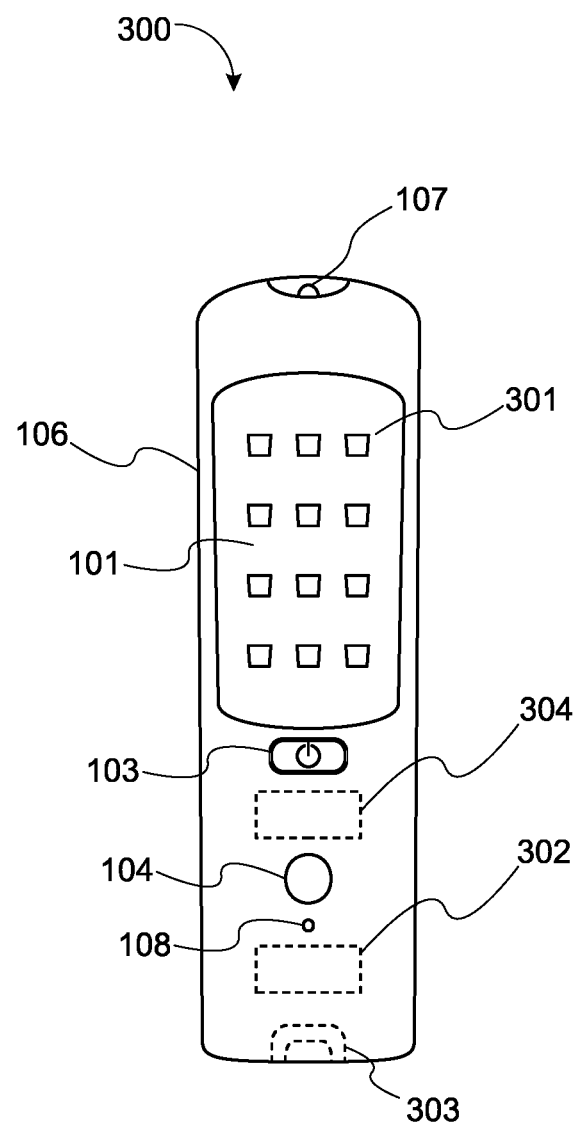
FIG. 3 illustrates a front view of a removeable emergency flashlight in accordance with at least one embodiment.

FIG. 3 illustrates a front view 300 of the presented removeable emergency flashlight in accordance with at least one embodiment. FIG. 3 depicts a light diffusing lens 101, a switch 103, a motion sensor 104, a removable emergency flashlight 106, an emergency light source 107, a photocell 108, a plurality of LEDs 301, an internal microprocessor 302, a charging port 303, and a rechargeable battery 304.

Figure 4A:
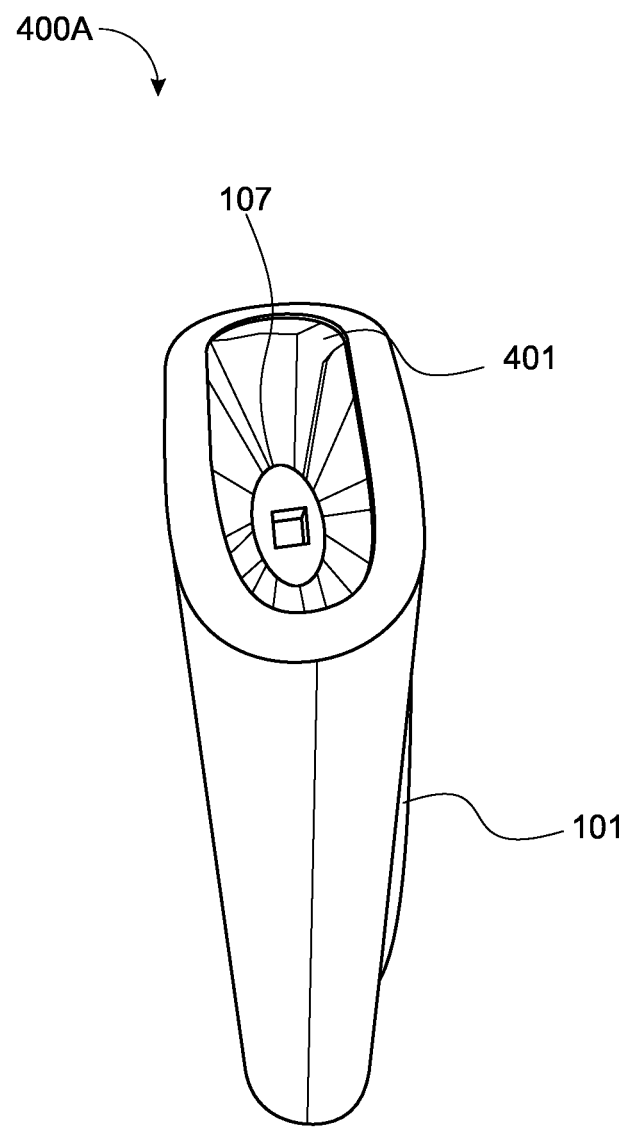
FIG. 4A illustrates a perspective view of a removable emergency flashlight in accordance with at least one embodiment.

FIG. 4A illustrates a perspective view 400A of the presented removeable emergency flashlight in accordance with at least one embodiment. FIG. 4A depicts a light diffusing lens 101, an emergency light source 107, and a reflector 401.

Figure 4B:
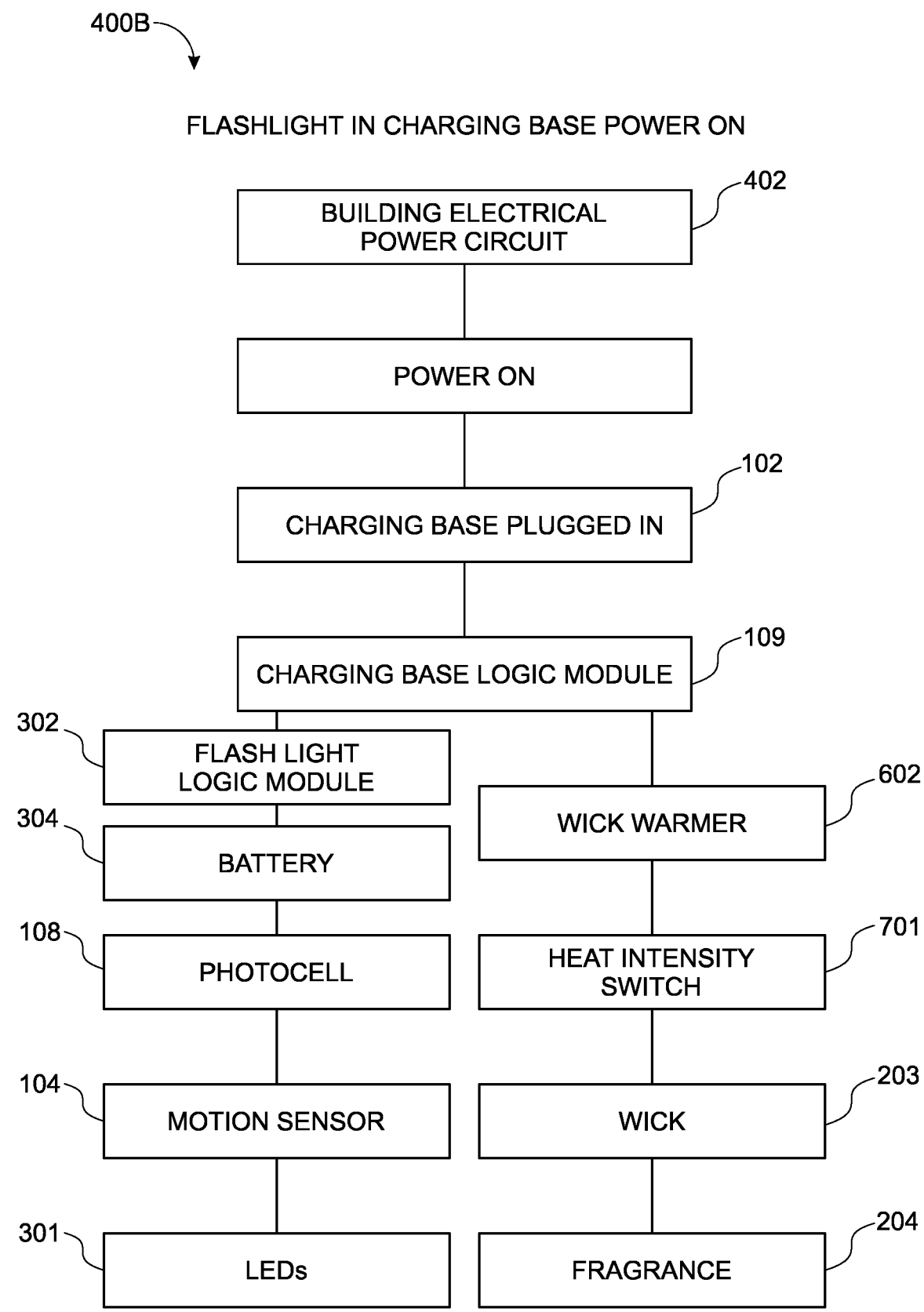
FIG. 4B is schematic drawing of the logic of the apparatus, when the removable emergency flashlight is sitting in the charging base, and the building's power is on, in accordance with at least one embodiment.

FIG. 4B is a schematic drawing 400B of the logic of the presented apparatus while the emergency removeable flashlight is stationary in the charging base, and a building's electrical power circuit is on, in accordance with at least one embodiment. FIG. 400B depicts a plugged-in charging base 102, a motion sensor 104, a photocell 108, a charging base microprocessor logic module 199, a wick 203, an airborne fragrance 205, a plurality of LEDs 301, a flashlight microprocessor logic module 302, a rechargeable battery 304, a building's electrical power circuit 402, a wick warmer 602, and a heat intensity switch 701.

Figure 4C:
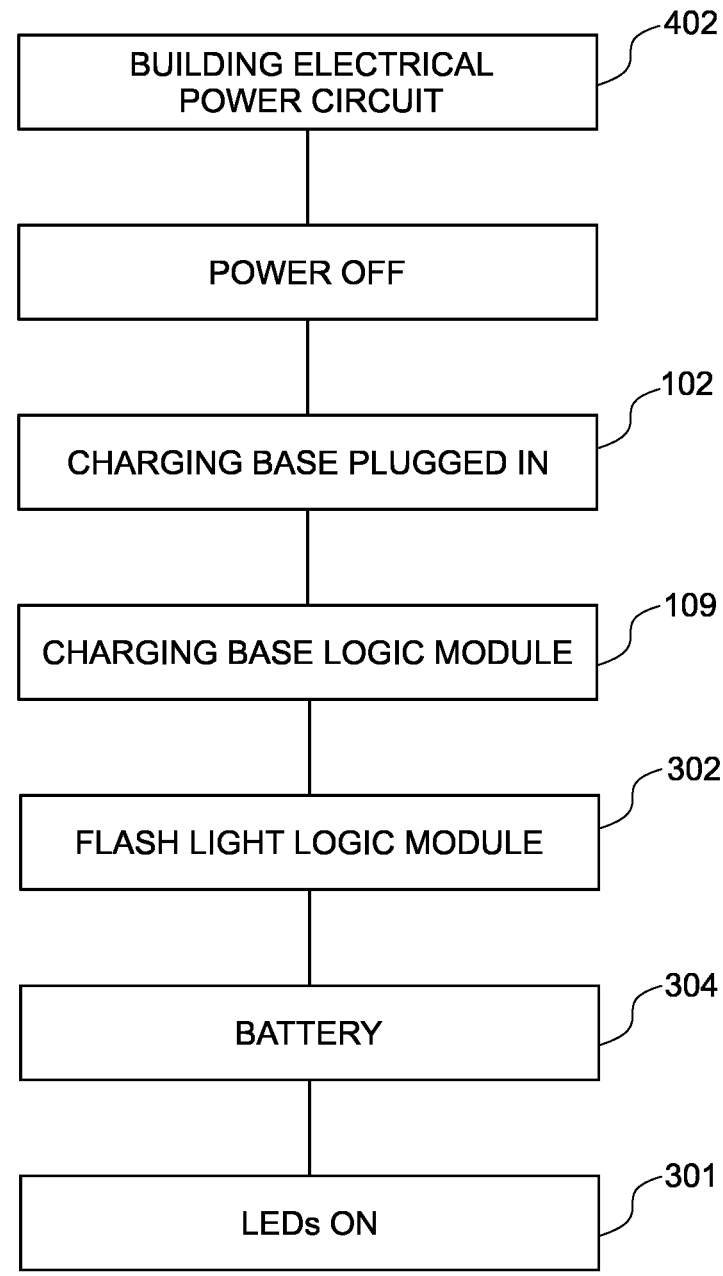
FIG. 4C is schematic drawing of the logic of the apparatus, when the removeable emergency flashlight is sitting in the charging base, and the building's power is off, in accordance with at least one embodiment.

FIG. 4C is a schematic drawing 400C of the logic of the presented apparatus while the emergency removeable flashlight is stationary in the charging base, and the building's power is off, in accordance with at least one embodiment. FIG. 400C depicts a plugged-in charging base 102, a charging base microprocessor logic module 109, a plurality of LEDs 301, a flashlight microprocessor logic module 302, a rechargeable battery 304, and a building's electrical power circuit 402.

Figure 4D:
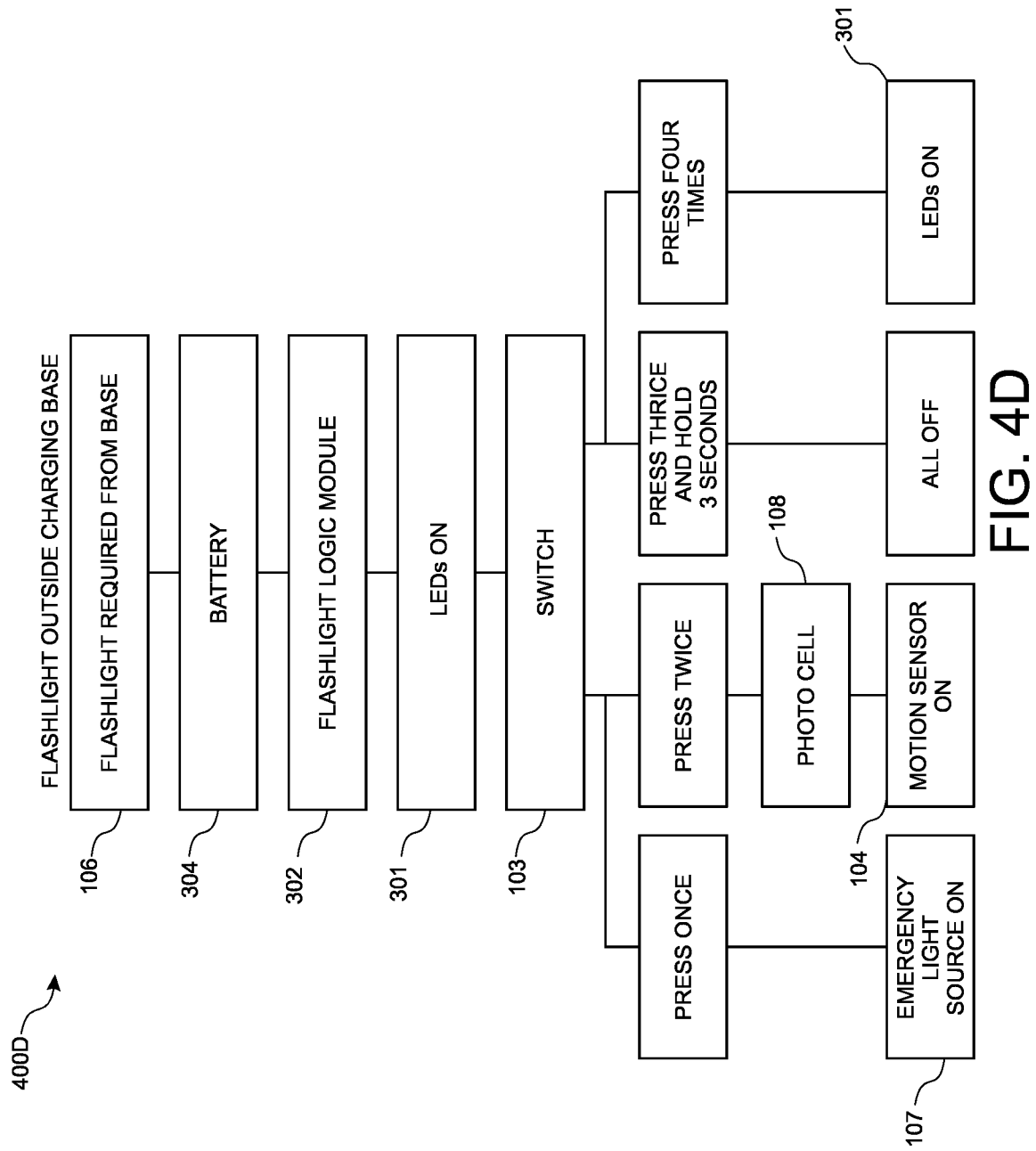
FIG. 4D is schematic drawing of the logic of the apparatus, when the removeable emergency flashlight is removed from the charging base, in accordance with, at least one embodiment.

FIG. 4D is a schematic drawing 400D of the logic of the presented apparatus while the emergency removeable flashlight is removed from the charging base, in accordance with at least one embodiment. FIG. 400D a switch 103, a motion sensor 104, an emergency removeable flashlight 106, an emergency light source 107, a photocell 108, a plurality of LEDs 301, a flashlight microprocessor logic module 302, and a rechargeable battery 304.

Figure 5:
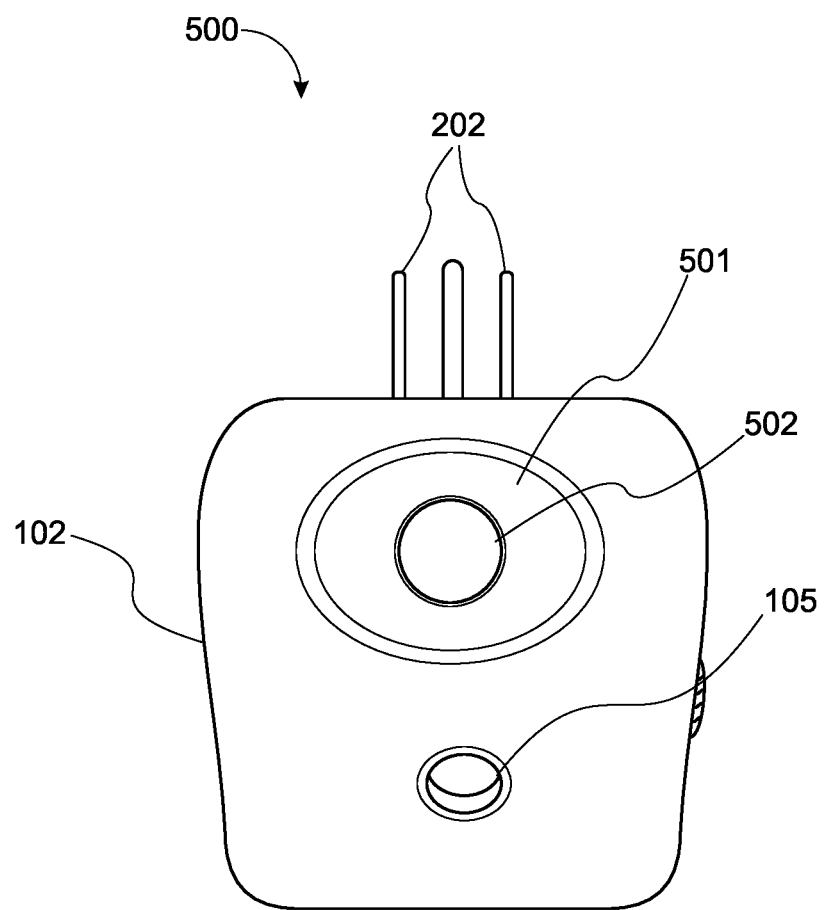
FIG. 5 illustrates a top view of the charging base, in accordance with at least one embodiment.

FIG. 5 illustrates a top view 500 of a charging base of the presented fragrance dispenser, with a removeable emergency flashlight, in accordance with at least one embodiment. FIG. 5 depicts a base 102, a base hole 105, a 3-prong plug 202, a charging station 501, and an induction charging post 502.

Figure 6:
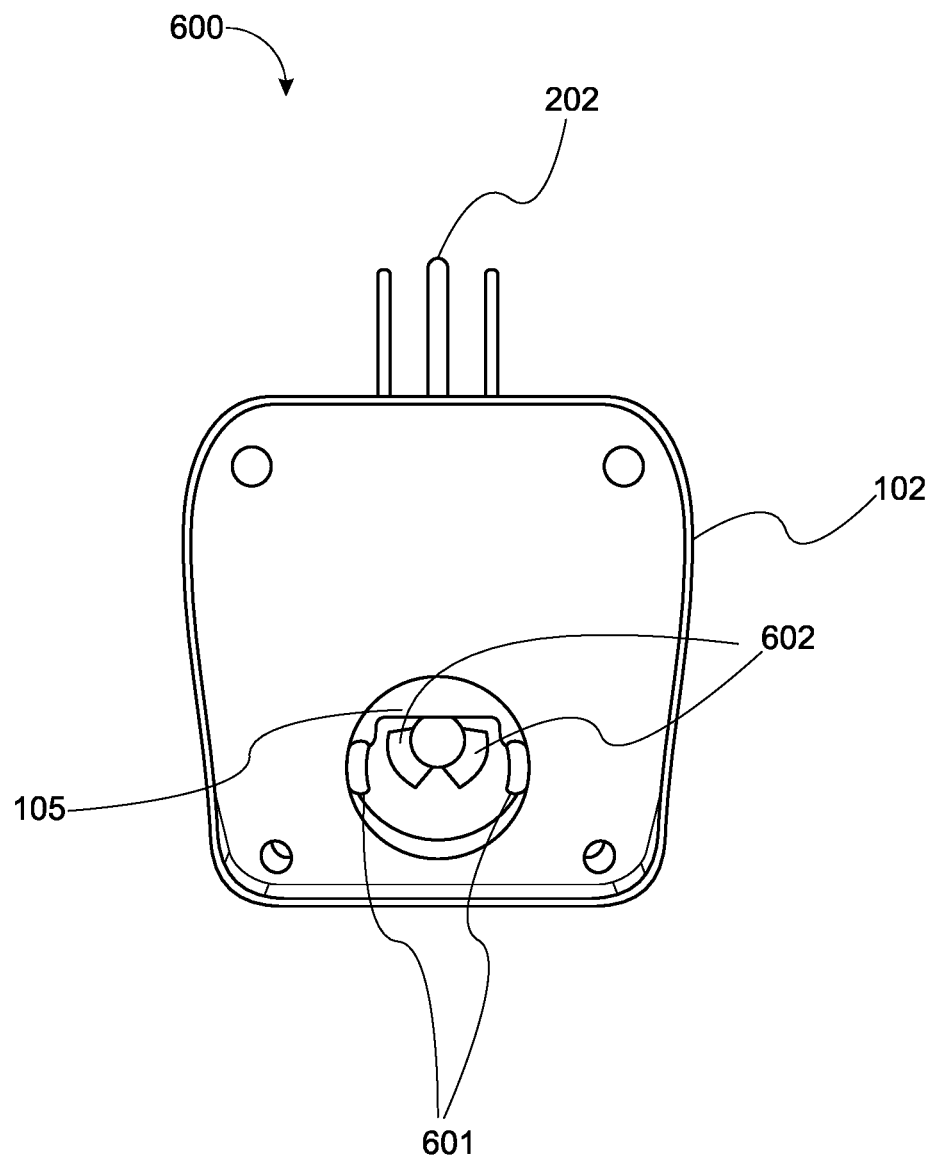
FIG. 6 illustrates a bottom view of the charging base, in accordance with at least one embodiment.

FIG. 6 illustrates a bottom view 600 of a charging base of the presented fragrance dispenser, with a removeable emergency flashlight, in accordance with at least one embodiment. FIG. 6 depicts a charging base 102, a charging base hole 105, a 3-prong plug 202, a fragrance bottle holder 601, and a wick warmer 602.

Figure 7:
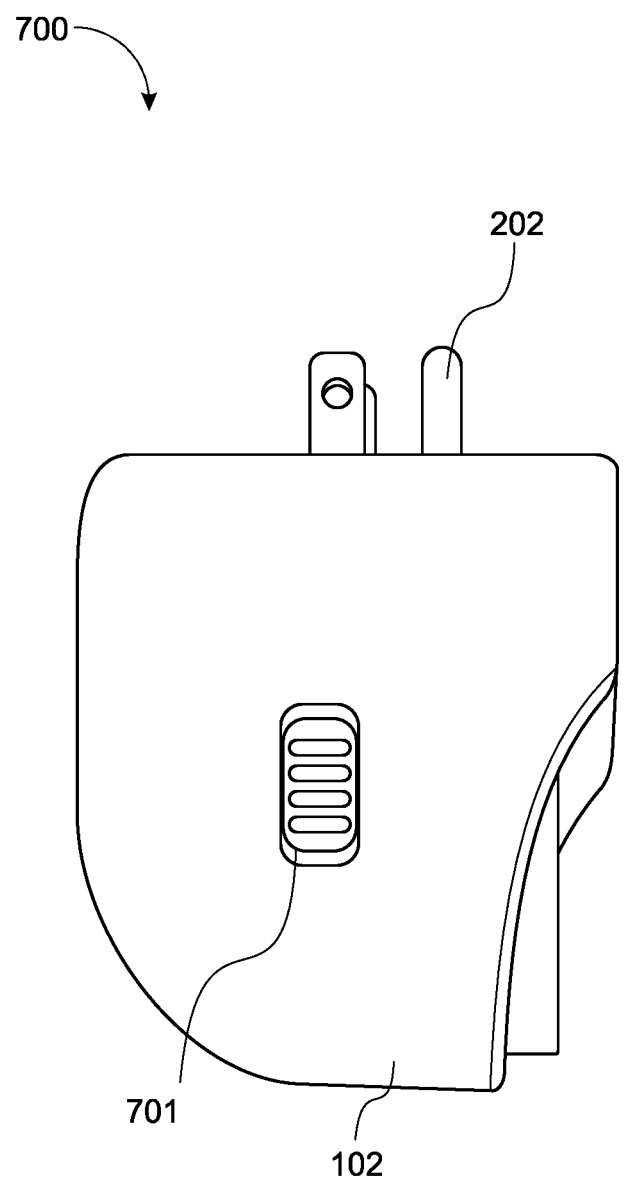
FIG. 7 illustrates a side view of the charging base, in accordance with at least one embodiment.

FIG. 7 illustrates a side view 700 of a charging base of the presented fragrance dispenser, with removable emergency flashlight, in accordance with at least one embodiment. FIG. 7 depicts a charging base 102, a 3-prong plug 202, and a heat intensity switch 701.

Figure 8:
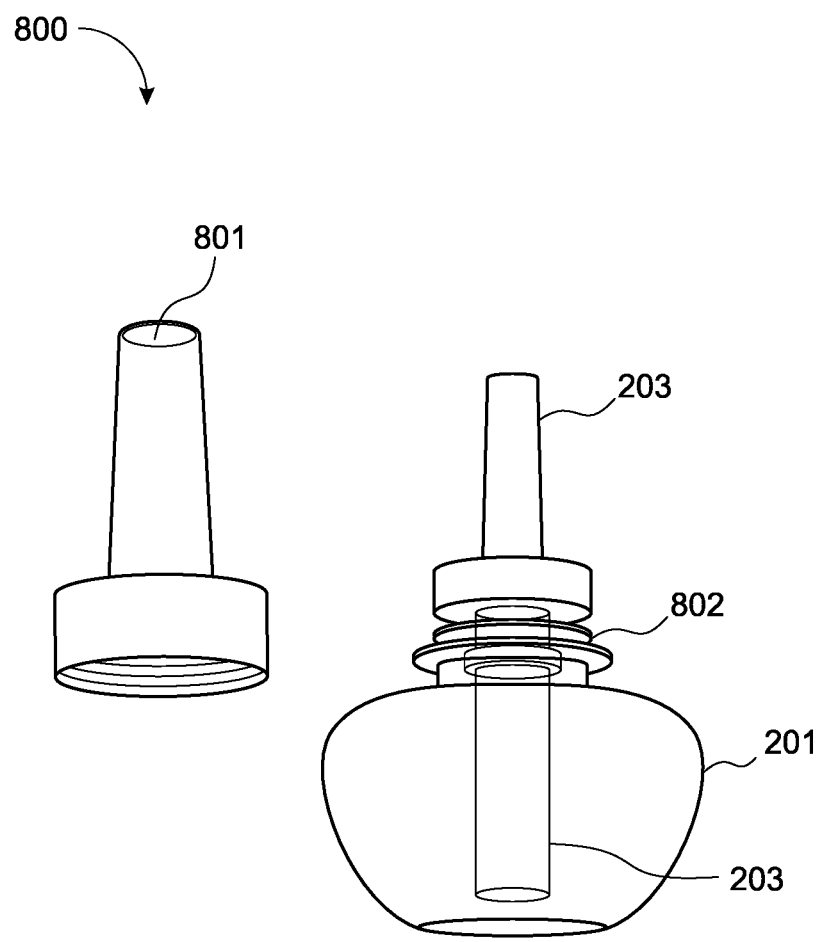
FIG. 8 illustrates a perspective view of a typical fragrance bottle, in accordance with at least one embodiment.

FIG. 8 illustrates a perspective view 800 of a typical fragrance bottle for use with the presented fragrance dispensing system, in accordance with at least one embodiment. FIG. 8 depicts a typical fragrance bottle 201, a wick 203, a bottle cap 801, and a threaded bottle neck 802.

It should be understood that light diffuser lens 101, can be made in varying sizes, shapes, configurations, and materials as determined by design.

It should be understood that bases 102 and 205 may or may not embody a heat intensity switch 701, and can be made in varying sizes, shapes, configurations, and materials as determined by design.

It should be understood that motion sensor 104 and photocell 108 can be made in varying sizes, shapes, designs, electrical parameters, configurations, operating areas and operating ambient light levels, as determined by design.

It should be understood that microprocessors 109 and 302 can be made in varying sizes, shapes, designs, configurations, components and each may or may not embody a photocell 108 and/or a motion sensor 104 into one PCBA (printed circuit board assembly), as determined by design.

It should be understood that emergency removeable flashlight 106 can be made in varying sizes shapes, configurations, and materials as determined by design.

It should be understood that emergency light source 107 can be one or a plurality of varying light sources, such as incandescent, LED, or fluorescent, in varying electrical parameters and configurations, as determined by design.

It should be understood that bottle 201 contains a wick 203, a bottle cap 801, and a threaded neck 802, all of which can be made in varying sizes, shapes, configurations, and materials as determined by design.

It should be understood that charging bases 102 and 205 may embody one of a 2-prong plug 202 or a 3-prong plug 206.

It should be understood charging bases 102 and 205, and can be made in varying sizes, shapes, configurations, and materials a determined by deign.

It should be understood that emergency removeable flashlight 106 can contain one or a plurality of rechargeable batteries 304, which rechargeable battery(s) can be made in varying sizes, shapes, configurations, and electrical parameters as determined by design.

It should be understood that emergency removeable flashlight 106 can embody one or a plurality of LEDs 301 which LEDs can be made in varying shapes, electrical parameters, and configurations, as determined by design.

It should be understood that emergency removeable flashlight 106 can embody a reflector 401, which reflector can be made varying sizes, shapes, configurations, and materials as determined by design.

It should be understood the wording "removeable emergency flashlight", "emergency removeable flashlight", "removeable flashlight", "emergency flashlight", and "flashlight" all have the same meaning and are all ascribed as to numeral 106 as shown in the detailed drawings.

In operation, the user inserts wick 203 into the hole in bottle 201 if such wick is not already in such hole, leaving the wick exposed. The bottle is inserted into bottle holder 601, through the bottom of the charging base hole 105 thereby allowing the wick to extend into the wick warmer 602. User inserts an attached 3-prong plug 202 or 2-prong plug 206 into a building's electrical power circuit 402. The user places the emergency removeable flashlight 106 into the charging station 501. Once the charging base is electrified, photocell 108 is engaged to determine the ambient light level and compare it to a predetermined light level. If the ambient light level is less than the predetermined light level the photocell will communicate with motion sensor 104. The motion sensor will activate and if motion is detected within its operating area, it will communicate with the charging base microprocessor logic module 109 to communicate with the flashlight microprocessor logic module 302 and such will illuminate the plurality of LEDs 301, acting as a night light. In the event of a power outage, the charging base microprocessor logic module will communicate with the flashlight microprocessor logic module, and such will illuminate the plurality of LEDs. Users may optionally remove the emergency removeable flashlight from the charging base. Once such flashlight is removed from charging base, users operate switch 103 to control the operation of the plurality of LEDs and emergency light source 107.

The above should not be used to limit the spirit and scope of our invention. It should be understood that our invention in not limited to the specific embodiments described in these specifications. Our invention is intended to cover many differing modifications and equivalent arrangements included within the spirit and scope of the invention as described in the claims. The scope of the claims is to be accorded the broadest interpretation so as to encompass such modifications, equivalencies, and functions.

The invention claimed is:

1. A plug-in apparatus comprising a fragrance dispenser, a night light, a motion sensor, and a removable emergency flashlight, wherein the plug-in apparatus further comprises:
   a charging base, that plugs into a building's electrical power circuit; and
   the charging base with a first embodied logic module, and connected with the fragrance dispenser to dispense fragrances, the fragrance dispenser including a heat intensity switch; and
   the removeable emergency flashlight comprising a charging logic module, further containing a plurality of LEDs and an emergency light source, wherein the removeable emergency flashlight is a flashlight logic module; and
   a motion sensor embodied within the removeable emergency flashlight, wherein the flashlight logic module is connected to the charging logic module to determine whether the building's electric power circuit is on or off, wherein the flashlight logic module recharges a battery and activates the motion sensor via the battery upon determining that the building's electrical power circuit is on, wherein the flashlight logic module illuminates the LEDs via the battery embodied within the removeable emergency flashlight upon determining that the building's electrical power circuit is off; and
   a photocell embodied within the removeable emergency flashlight.

2. The apparatus according to claim 1, wherein the fragrance dispenser dispenses fragrance using a wick warmer to evaporate a fragrance liquid contained in a fragrance bottle which is absorbed by a wick.

3. The apparatus according to claim 1, wherein the heat intensity switch is embodied within the charging base, and the heat intensity switch regulates the amount of fragrance dispensed by the fragrance dispenser; and, wherein the heat intensity switch further regulates both an amount of heat received by the wick and the amount of heat received by the wick determines the evaporation rate of said wick.

4. The apparatus according to claim 1, wherein the charging base embodies the charging logic module, and the charging logic module determines whether the building's electrical power circuit is on or off.

5. The apparatus according to claim 1 wherein the charging logic module continually communicates a state of the building's electrical power circuit to the charging logic module contained in the removeable emergency flashlight when the removeable emergency flashlight is seated in the charging station.

6. The apparatus according to claim 4, wherein the charging logic module senses whether a state of the building's electrical power is on or off; when the charging module senses the state as on, the charging logic module keeps the wick warmer in a powered-on state and communicates to the flashlight logic module the powered-on state of the wick warmer.

7. The apparatus according to claim 5, wherein the flashlight logic module receives constant communication from the charging logic module as to whether the state of the building's electric power circuit is on or off.

8. The apparatus according to claim 1, wherein the removeable emergency flashlight embodies a switch, and the switch controls an operation of the LEDs and the emergency light source while the removeable emergency flashlight is not seated in the charging station.

9. The apparatus according to claim 1, wherein the removeable emergency flashlight embodies the photocell, wherein the photocell is configured to sense an ambient light level and compare it to a predetermined light level and alter a state of the motion sensor as a function of the ambient light level.

10. The apparatus according to claim 9, wherein when the state of the motion sensor has been altered by the photocell, the photocell is configured to activate the motion sensor when the photocell determines that the ambient light level is below the predetermined level.

11. The apparatus according to claim 8, wherein when the removeable emergency flashlight is removed from the charging station, the LEDs of the removeable emergency flashlight are turned on and are controlled by the switch, whether or not the building's electrical power circuit is on or off.

12. The apparatus according to claim 1, wherein the removeable emergency flashlight is capable of being removably coupled to the charging station.

\* \* \* \* \*